(12) United States Patent
Trammell et al.

(10) Patent No.: US 7,193,142 B2
(45) Date of Patent: Mar. 20, 2007

(54) CELERY VARIETY COMMAND

(75) Inventors: Keith W Trammell, Nipomo, CA (US); Robert E. Pybas, Santa Maria, CA (US)

(73) Assignee: Pybas Vegetable Seed Co., Inc., Santa Maria, CA (US)

( * ) Notice: Subject to any disclaimer, the term of this patent is extended or adjusted under 35 U.S.C. 154(b) by 0 days.

(21) Appl. No.: 11/125,426

(22) Filed: May 9, 2005

(65) Prior Publication Data

US 2006/0253941 A1    Nov. 9, 2006

(51) Int. Cl.
*A01H 5/00* (2006.01)
*A01H 5/10* (2006.01)
*C12N 15/82* (2006.01)

(52) U.S. Cl. .................. 800/318; 800/298; 435/410
(58) Field of Classification Search ............... 800/260, 800/318; 435/410
See application file for complete search history.

(56) References Cited

U.S. PATENT DOCUMENTS

| | | | | |
|---|---|---|---|---|
| 5,304,719 A | * | 4/1994 | Segebart | 800/303 |
| 5,367,109 A | * | 11/1994 | Segebart | 800/320.1 |
| 5,763,755 A | * | 6/1998 | Carlone | 800/320.1 |
| 5,850,009 A | * | 12/1998 | Kevern | 800/271 |
| 6,818,810 B2 | * | 11/2004 | Pierce | 800/318 |

OTHER PUBLICATIONS

Browers and Orton 1986, Biotechnology in Agriculture and Forestry vol. 2: Crops I, edited by Y.P.S. Bajaj, Springer-Verlag, Berlin, Heidelberg, pp. 405-420.*
Quiros et al 1987, Plant Cell Reports 6: 114-117.*

* cited by examiner

*Primary Examiner*—David H. Kruse
*Assistant Examiner*—Keith O. Robinson
(74) *Attorney, Agent, or Firm*—DLA Piper US LLP

(57) ABSTRACT

A new variety of celery given the name "Command" and whose seed has an ATCC number PTA-6627 is presented. Command exhibits a set of characteristics that is different from its parents, Matador and 85-6-3. In addition to the Command plant and its seed, a method of producing a hybrid celery plant by crossing a Matador plant with an 85-6-3 plant is also presented.

3 Claims, No Drawings

CELERY VARIETY COMMAND

FIELD OF THE INVENTION

This invention relates generally to the field of plant breeding and in particular to a new variety of celery.

BACKGROUND

The commercial vegetable crop known as celery is widely used in cooking a variety of dishes and is frequently eaten without cooking, as a light snack. There are a number of varieties of celery crops. Although these crops of the celery family generally share a similar look and flavor, they differ in specific traits such as petiole size, shape, and number, succulence, ribbiness, disease resistance, shelf life, and bolting pattern, among others.

These specific traits make a celery variety more or less appealing from a commercial standpoint. For example, a variety that is disease resistant and has a longer shelf life is likely to be more commercially valuable than a variety that is susceptible to diseases or has a short shelf life. Also, since the parts of a celery plant that are most commonly consumed are the petioles (or the "stalks"), a variety that produces more petioles is likely to be more desirable than a variety that produces fewer petioles.

While the pursuit to produce a celery variety that is more appealing for farmers and stores is on-going, it is important that the new varieties retain the flavor, texture, and nutritional properties of the parent plant that is desired by consumers. Thus, search continues for a celery variety that is appealing for consumption while presenting economic advantages to farmers and stores.

SUMMARY

The invention is a variety of celery whose seed has an ATCC number PTA-6627. The plant from this seed is given the name "Command." Command exhibits a set of characteristics that is different from any currently-existing celery variety. Being a cross between Matador and 85-6-3, Command shows strong fusarium resistance similar to Matador.

In addition to the plant and the seed, the invention includes a progeny, a clone, and a somaclone of a Command celery plant. The invention also includes a regenerable tissue culture of a Command celery plant.

The invention is further directed to a method of producing a hybrid celery plant by crossing a Matador plant with an 85-6-3 plant.

DETAILED DESCRIPTION OF THE INVENTION

The crop of the invention is a member of *Apium graveolens L.* of the family *Umbelliferae*.

Cross Between Matador and 85-6-3

Command (PYC 2531) is a result of a cross between the celery varieties Matador and a slow-bolting selection from the variety Napoleon generally referred to as 85-6-3. A petiole from the Matador was placed into an appropriate growth medium. The petiole that is placed is sterilized prior to culture to prevent growth of contaminating microorganisms, and then rinsed two or three times with sterile distilled water.

The individual flowers in celery are extremely small and difficult to hand-pollinate. Thus, controlled crosses are made by taking advantage of the protandrous nature of the species (i.e., the pollen matures before the stigmas on the same flower).

The inflorescence in celery is a compound umbel. It is comprised of a number of smaller umbellets, which in turn are made up of several tiny individual flowers. The umbellets arranged around the perimeter of the larger umbel bloom earlier than those at its center and the individual flowers at the outer edges of a given umbellet tend to bloom a day or two before those at the center of the umbellet.

In preparing for a cross, an umbel just starting to bloom is selected on the plant intended as the female. The less mature umbellets near the center of the umbel are removed with a pair of forceps along with three buds that would otherwise give rise to the next order of umbels. Then, among the few remaining outside umbellets, the slower blooming centermost individual flowers are removed, leaving a concentration of individual flowers all at the similar stage of development.

Thus prepared, the female is enclosed in a paper bag to exclude any unwanted sources of contaminating pollen. After approximately 4–5 days in which the pollen has all been shed and is no longer viable, the paper bag is removed and the stigmas are examined to see if they have yet become receptive. If the stigmas are receptive, a number of stems with some fresh bloom and some unopened flowers are cut from the intended male plant and placed in a jar of water to provide fresh pollen for a period of several days. These flowers are then enclosed inside the same paper bag with the receptive female and is shaken daily to keep the pollen stirred up to assure cross pollination.

After about a week, the flowers from the male plant are discarded. The ovaries on the female can be seen to swell in about two weeks. Then, after about four more weeks, they start changing from green to tan and eventually brown in color, at which time the F1 seed can be harvested.

Population Selection

The F1 seeds were harvested in late summer of Year 1, a few months after Matador and 85-6-3 were crossed. The F1 seeds were planted indoors a few weeks after the harvest, transplanted to outdoor pots in the winter (January of Year 2), and induced to bolt that winter. The F1 seeds flowered, were caged singly, and F2 seeds were harvested in the October of Year 2.

In the spring of Year 3, seedlings of the F2 seeds were transplanted to Lompoc, Calif. that was heavily infested with fusarium. Several highly fusarium-resistant F2 plants with good horticultural features were selected, and set out in pots in Santa Maria, Calif. over the winter. In the summer of Year 4, the plants were caged separately and F3 seeds were harvested in the fall of Year 4.

The several F3 lots were seeded shortly after the harvest, and transplanted into a bolting trial in Lompoc in January of Year 5. A few non-bolting plants from the slowest bolting lines were selected and transplanted into pots in April of Year 5. These plants were held over through the winter and flowered in the summer of Year 6. The F4 seeds were harvested in October of Year 6.

Within a few weeks of the harvest, the F4 seeds were planted for a bolting trial, and were transplanted to the field in January of Year 7. There was segregation within lines and between lines by petiole smoothness and thickness, compactness, stalk diameter, and bolting ease. One line was quite uniform and consistently produced crops of large diameter stalks. Two outstanding non-bolting plants from this line were selected in April of Year 7, and were held in pots and overwintered outdoors. The two outstanding plants were caged singly in the summer of Year 8 and F5 seeds were obtained from them.

The F5 seeds obtained from the two outstanding plants were seeded and transplanted to Santa Maria, Calif. that had been heavily infested with fusarium for years. The seeds from both plants were the same in type and showed improved fusarium resistance compared to the parents. They also produced good size crops. Of the two plots, the one that is judged to be the most uniform was given the experimental designation PYC 2531. Some leftover F5 seeds (PYC2531) were trailed in Year 9 and confirmed to be uniform and stable.

Six seeds were selected from PYC 2531, potted, and overwintered through the end of Year 9 and early Year 10 for cold induction. They were flowered and massed together in a large cage in the summer of Year 10, producing F5M seed that was harvested in October of Year 10. In Year 11 and Year 12, PYC 2531 with the F5M lot produced in Year 10 were trailed.

In Year 12, a first commercial seed production crop of PYC 2531 was grown in Lompoc, Calif. This line was trailed for a few years to confirm that a consistent uniformity and stability were observed in the crops, and PYC 2531 was named "Command."

Command Characteristics

Command is most similar to the variety Matador, its female parent. Matador and Command are both highly fusarium-resistant, have petioles of equal width and thickness, and are fairly similar from each other in weight of the trimmed stalks. However, there are differences, as summarized in Table 1. As shown in the table, Command is shorter in height than Matador and has a shorter petiole length to the first node. As far as the overall height and the petiole length are concerned, Command resembles the Sonora variety more than it resembles Matador. Command has a greater number of inner and outer petioles than Matador. Also, Command is slower to bolt than Matador in terms of the length of its seedstem when grown under bolting conditions (seedstems ≦ 15 cm is considered to have "bolted"). In one experimental season, 13% less of the Command bolted than of Matador. Command's bolting resistance is closer to that of T.U. 52–75 than to that of Matador.

TABLE 1

General Comparison of Command and Matador

|  | Average Measurements | |
| --- | --- | --- |
|  | Command | Matador |
| Height | 70–79 cm (mean = 76.6) | 80.4 cm |
| Petiole Length to first node | 26–33 cm (mean = 28.9) | 32.4 cm |
| No. of Inner Petioles | 4.6 | 3.5 |
| No. of Outer Petioles | 11 | 9.8 |
| Reaction to *Fusarium oxysporum* | resistant | resistant |

The petioles were about medium (about 21 mm) in width and about 20 mm in thickness at the midpoint between the first joint and the wing. The petioles were moderately cupped at the midpoint, and the petiole was generally of dark green color. The ribbing on the petioles are moderate, as was the level of glossiness. The leaf blades of the outermost petioles were dark green in color.

EXAMPLE 1

Table 2 summarizes the results of Trial 1 that took place in Santa Maria, Calif. between 2003 and 2004. The seeds were planted indoors on Oct. 16, 2003, transplanted to a field on Aug. 15, 2004, and harvested on Nov. 18, 2004. The sample size was 12 plants. For the ANOVA, F(req'd) 0.05=10.13, and F(req'd) 0.01=34.12.

TABLE 2

Comparison of Command and Matador in Trial 1

|  | Measurements | | |
| --- | --- | --- | --- |
|  | Command | Matador | ANOVA (Command) |
| Stalk weight (g) | 1010 ± 49.1 | 1004 ± 26 | F(calc.) = 0.05 NS |
| Plant height (cm) | 81.9 ± 1.6 | 87.9 ± 0.6 | F(calc.) = 64.8** |
| Petiole length (cm) | 32.4 ± 1.2 | 36.6 ± 0.6 | F(calc.) = 63.3** |
| No. Outer Petioles | 11.4 ± 0.4 | 9.9 ± 0.5 | F(calc.) = 17.1* |
| No. Inner Petioles | 4 ± 0.2 | 3.2 ± 0.1 | F(calc.) = 128** |
| Petiole Width (mm) | 21 ± 0.5 | 21.1 ± 0.5 | F(calc.) = 0.04 NS |
| Petiole Thickness (mm) | 10.6 ± 0.5 | 10.7 ± 0.3 | F(calc.) = 0.19 NS |

EXAMPLE 2

Table 3 summarizes the results of Trial 2 that took place in Los Alamos, Calif. in 2004. The seeds were planted indoors on Feb. 6, 2004, transplanted to a field on Apr. 17, 2004, and harvested on Jul. 12, 2004. The sample size was 12 plants. For the ANOVA, F(req'd) 0.05=10.13, and F(req'd) 0.01=34.12.

TABLE 3

Comparison of Command and Matador in Trial 2

|  | Measurements | | |
| --- | --- | --- | --- |
|  | Command | Matador | ANOVA (Command) |
| Stalk weight (g) | 1021 ± 115 | 873 ± 46.8 | F(calc.) = 7.57 NS |
| Plant height (cm) | 69.2 ± 1.4 | 72.8 ± 1.6 | F(calc.) = 4.95** |
| Petiole length (cm) | 25.3 ± 0.9 | 28.2 ± 0.9 | F(calc.) = 36.8** |
| No. Outer Petioles | 10.6 ± 0.3 | 9.7 ± 0.4 | F(calc.) = 25.6* |
| No. Inner Petioles | 5.2 ± 0.5 | 3.8 ± 0.3 | F(calc.) = 19.1** |
| Petiole Width (mm) | 21.5 ± 1.5 | 20.5 ± 0.9 | F(calc.) = 3.0 NS |
| Petiole Thickness (mm) | 9.8 ± 0.4 | 9.7 ± 0.4 | F(calc.) = 0.2 NS |

EXAMPLE 3

Table 4 summarizes the results of a bolting speed comparison between Command and Matador that took place in Santa Maria, Calif. in 2003–2004. The seeds were planted indoors on Oct. 16, 2003, transplanted to a field on Jan. 5, 2004, and evaluated on May 4, 2004 for bolting speed. The sample size was 12 plants. For the ANOVA, F(req'd) 0.05=10.13, and F(req'd) 0.01=34.12.

TABLE 4

Comparison of Bolting Speed between Command and Matador

| | Measurements | | |
|---|---|---|---|
| | Command | Matador | ANOVA (Command) |
| Seed stem length (cm) | 19.9 ± 0.3 | 27.1 ± 2.4 | F(calc.) = 47.2** |

In Tables 2, 3, and 4, "NS" indicates that there is no significant difference between the means, "*" indicates that the difference between the means is significant at 0.05 probability level, and "**" indicates that the difference between the means is significant at 0.01 probability level.

Although the foregoing invention has been described in some detail by way of illustration and examples for purposes of clarity and understanding, it will be obvious that certain modifications and alternative embodiments of the invention are contemplated which do not depart from the spirit and scope of the invention as defined by the foregoing teachings and appended claims.

What is claimed is:

1. A seed of celery cultivar "Command", wherein a representative sample of seed has been deposited under ATCC accession number PTA-6627.

2. A celery plant having all of the characteristics of a plant produced by seed deposited with the American Type Culture Collection and assigned accession number PTA-6627.

3. A tissue culture of regenerable cells of the plant of claim 2.

* * * * *